United States Patent [19]

Wagener et al.

[11] Patent Number: 4,630,479

[45] Date of Patent: Dec. 23, 1986

[54] SAMPLING DEVICE FOR SOLIDS IN A PRESSURIZED REACTOR

[75] Inventors: Heinrich Wagener, Bochum; Reinhold Kirchhoff, Hattingen; Karl H. Van Heek; Harald Jüntgen, both of Essen, all of Fed. Rep. of Germany

[73] Assignee: Bergwerksverband GmbH, Essen, Fed. Rep. of Germany

[21] Appl. No.: 735,415

[22] Filed: May 17, 1985

[30] Foreign Application Priority Data

May 17, 1984 [DE] Fed. Rep. of Germany ....... 3418311

[51] Int. Cl.$^4$ .............................................. G01N 1/04
[52] U.S. Cl. .................................................. 73/863.83
[58] Field of Search ........... 73/863.83, 863.11, 863.81, 73/863.82, 864, 864.31, 864.34, 864.73

[56] References Cited

U.S. PATENT DOCUMENTS

| | | | |
|---|---|---|---|
| 2,615,339 | 10/1952 | Holgersson et al. | 73/863.82 |
| 3,129,590 | 4/1964 | Ellis | 73/863.83 |
| 3,487,695 | 1/1970 | Haunschild et al. | 73/863.81 |
| 3,490,289 | 1/1970 | Mangin | 73/864.31 |
| 3,541,860 | 11/1970 | George | 73/863.83 |
| 3,643,508 | 2/1972 | Schneider | 73/863.83 |
| 3,726,143 | 4/1973 | Enarsson | 73/863.83 |
| 3,949,614 | 4/1976 | Abonnenc | 73/863.83 |
| 4,009,618 | 3/1977 | Chatham | 73/863.83 |
| 4,262,533 | 4/1981 | Jaeger | 73/863.83 |
| 4,355,539 | 10/1982 | Schatz | 73/863.11 |
| 4,433,587 | 2/1984 | Risdal | 73/863.83 |

FOREIGN PATENT DOCUMENTS

1934028 1/1971 Fed. Rep. of Germany ... 73/863.11

Primary Examiner—Stewart J. Levy
Assistant Examiner—Robert R. Raevis
Attorney, Agent, or Firm—Karl F. Ross; Herbert Dubno

[57] ABSTRACT

A sampling device for solids from a pressure reactor includes a housing which is connected to the reactor and accommodates a tube with its one end opening into the reactor. Movable within the tube is a sampling piston which is provided with gas-impermeable piston rings. To withdraw solids from the reactor, the piston is moved into the reactor such that the forward piston ring projects into the chamber of the reactor and is then retracted with a solids sample arranged in between the piston rings. The piston is moved to an opening of the tube so that the solids sample can be discharged to the outside.

9 Claims, 14 Drawing Figures

SAMPLING DEVICE FOR SOLIDS IN A PRESSURIZED REACTOR

FIELD OF THE INVENTION

Our present invention refers to a sampling device for solids from a pressure reactor.

BACKGROUND OF THE INVENTION

In chemical and physical processes, especially in pyrolysis and gasification reactions occurring in pressurized fluidized-bed reactors, it is desirable to have knowledge about the chemical and physical modifications of the grain e.g. of carbon (coal) grains within the fluidized bed, because the hydrodynamic conditions of the fluidized bed are dependent on the grain size changes. Such examinations have been conducted to date only in laboratory tests.

OBJECTS OF THE INVENTION

The principal object of our present invention is thus to provide a sampling device which allows a direct removal of solids from the hot fluidized bed with unaltered chemical and physical properties and undamaged grain structure of the sample.

Another object is to provide a sampling system which can provide truly representative samples in a pressurized reactor.

SUMMARY OF THE INVENTION

These objects are realized according to the present invention by providing a sampling device which includes a housing connected to the reactor and accommodating a piston with gas-permeable rings which is movable within a tube in an axial direction between a first position in which solids are withdrawn from the reactor and a second position in which the withdrawn solids are discharged through an opening of the tube to the outside. The tube is anchored in a wall of the pressurized fluid-bed reactor and has an end opening at the interior of this wall.

For providing an overpressure inside and outside the tube to prevent solids from penetrating into the tube behind the piston, a plurality of gas lines are connected to the housing through which sealing (barrier) gas and, if desired, flushing and cooling gas can be introduced. The barrier gas can also serve as flushing and cooling gas.

The solids sample after being withdrawn by the piston is discharged through a funnel to a double sluice (gate or lock) arrangement with intermediate sliders and shutters and finally accumulated within a collector.

Through the provision of a sampling device according to the invention, it is possible to withdraw the hot solids sample from the reactor and to remove aggressive crude gas fractions by flushing and simultaneously to cool the solids during the transport from the reactor to the discharge location. In an idle position, the continuously flowing stream of flushing gas prevents a penetration of crude gas and solids into the sampling piston.

For moving the piston in axial direction, a piston rod is connected thereto and extends beyond the housing with its rear portion. Connected to the rear portion of the piston rod is a winch which upon actuation moves the piston rod via a rope or cable (flexible element) and thus the piston back and forth. For providing an exact guidance of the piston rod, its rear portion is supported by a roller track which includes a plurality of rollers.

According to a further feature of the present invention, the piston includes two spaced gas permeable piston rings which are each provided with a plurality of plates arranged at a distance to each other so that between adjacent pairs of plates gas-permeable insulating material can be inserted.

BRIEF DESCRIPTION OF THE DRAWING

The above and other features, objects and advantages of our invention will become more readily apparent from the following description, reference being made to the accompanying drawing in which.

SPECIFIC DESCRIPTION

Referring to the drawing, there is shown a sampling device 100 arranged at an outer metallic reactor wall 21 of an otherwise not illustrated pressure vessel 23. In the present example, a fluidized pressurized reactor 23 is used in whose interior finely divided solids (coal) are suspended in a current of water vapor (steam) at a maximum temperature of 850° C. and at a pressure of 40 bar to produce a fluidized bed 28. Along its inner side, the reactor wall 21 is coated with a lining 22 of insulating masonry.

At a predetermined position, the reactor wall 21 and the lining 22 is traversed by a passage 63 which allows access of the sampling device 100 to the fluidized bed 28 so that samples of solids can be extracted from within the reactor 23, as will be described hereinafter.

The sampling device 100 extends perpendicularly to the reactor wall 21 and includes a bottle-shaped housing 1 whose interior is divided in a rearward chamber 34 and a forward chamber 34a by a partition wall 39. At its end facing the reactor wall 21, the housing 1 is provided with a flange 1a which is in connection, e.g. by means of screws, with the opposing flanged portion 2a of a union 2 whose other end is connected to the reactor wall 21.

The union 2 is connected to the reactor wall 21 such that its through-opening 80 is in alignment with the passage 63.

Consequently, the fluidized bed 28 within the reactor 23 is in communication with the interior of the housing 1.

Traversing the passage 63 is a double-wall pipe 25 whose one end is exposed towards the fluidized bed 28 and essentially flush with the inner surface of the lining 22. The other end of pipe 25 extends into the union 2 and is tightly welded to the latter in order to prevent bypass flows in the union 2. The double-wall pipe 25 defines an inner chamber 32 filled with insulating material e.g. highly temperature-resistant wool of $Al_2O_3$ and acts as a sliding sleeve for one end section of an elongated tube 27. The tube 27 which is thus partly embraced by the inner diameter of the pipe 25 extends into the housing 1 and is tightly welded within the partition wall 39. Since the tube 27 as well as the double pipe 25 are exposed with their respective end towards the fluidized bed 28, flexibility is provided to expand in case of temperature fluctuations.

Figure 9:
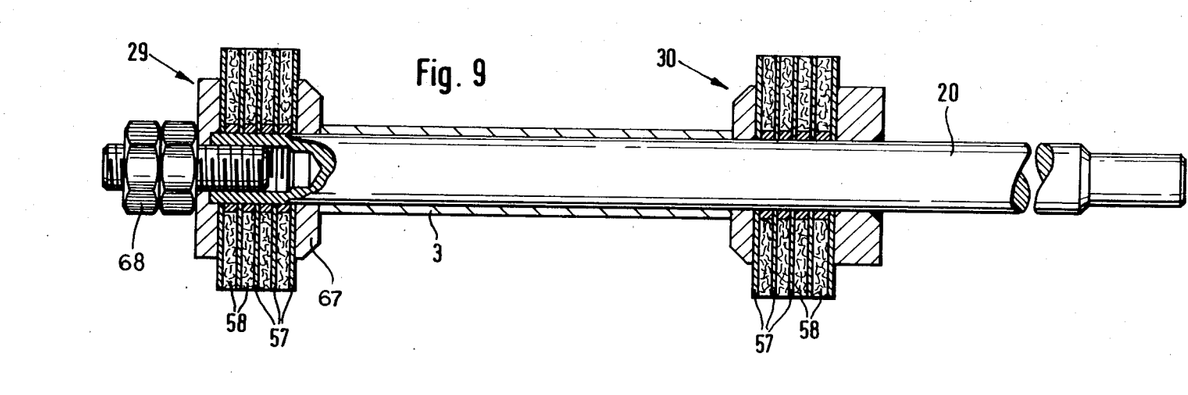
FIG. 9 is a longitudinal sectional view of a sampling piston.
Figure 10:
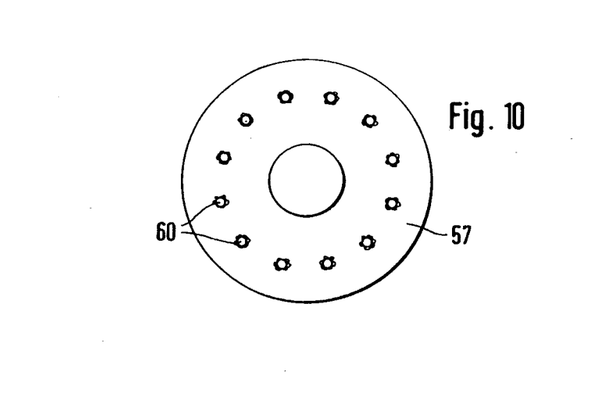
FIG. 10 is an elevation of one piston plate of a piston ring of the sampling piston.

Running within the tube 27 is a sampling piston 3 which is illustrated in greater detail in FIG. 9. Accordingly, the piston 3 is provided with a front gas permeable piston ring 29 directed towards the fluidized bed 28 and a rear gas permeable piston ring 30 each of which being constituted by five parallel circular plates 57 arranged at a distance to each other. The plates 57 which are retained in relationship to each other by a clamp 67 and a bolt joint 68 are made of highly temperature-resistant material e.g. Incoloy 800. Accommodated in a tight manner within the spaces inbetween adjacent plates 57 are insulating fiber mats 58 made of $Al_2O_3$. To provide a tight fit of the fiber mats 58, the plates 57 are provided with a plurality of punched and non-deburred holes 60. Such a design of the piston rings 29, 30 prevents a seizing of the piston 3 because the solids particles deposit in the soft and elastic insulation as provided by the fiber mats 58.

The piston 3 is movable within the tube 27 by a piston rod 20 which acts on the rear piston ring 30. The piston rod 20 extends through the tube 27 and is supported and driven from outside the housing 1 as will be described hereinbelow.

At a section extending in the forward chamber of the housing 1, the tube 27 is provided with an opening 69 which registers with a discharge funnel 37 extending to the outer wall of the housing 1. The funnel 37 defines a chamber 59 which communicates with the interior tube 27 via opening 69. At its lower open end, the funnel 37 is connected to an outlet pipe 70 which forms part of a connecting piece 71 welded to the outer wall of the housing.

To ensure the transfer of solids from the chamber 59 to pipe 70, the respective ends of the funnel 37 and the pipe 70 overlap each other.

Figure 1:
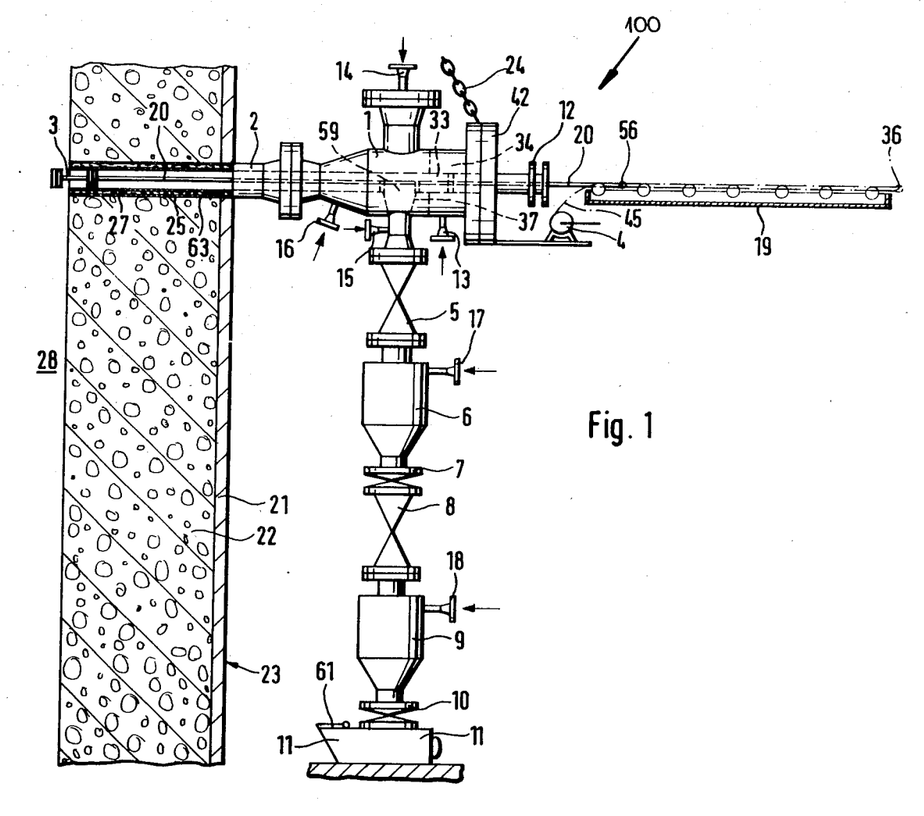
FIG. 1 is a schematic elevational view of a sampling device according to the invention connected to a pressure reactor (shown in section)

As is shown in FIG. 1, the outlet pipe 70 leads to a first slider 5 to which a first sluice (gate or lock) 6 with a gas inlet 17 and a first shutter 7 is connected. Via a second slider 8, a second sluice (gate or lock) 9, a gas expansion line 18 and a second shutter 10, the sample of solid material is discharged into a collector 11 which is equipped with a hinged filter cover 61.

Connected to the rear chamber 34 is a fitting 13 through which sealing gas can be supplied which serves also as flushing or cooling gas. Likewise, the forward chamber 34a communicates with a line 16 and outlet pipe 70 with a line 15 for allowing a supply of flushing and cooling gas. As is shown in FIG. 3, the housing 1 is provided with further connections 40, 41 through which gas can be fed.

Opposite the opening 69, the tube 25 is provided with a further opening 72 which is closed by a sealing plug 26. Embraced by the sealing plug 26 is a connecting pipe 14 through which additional flushing and cooling gas can be supplied. The sealing plug 26 is loaded by a spring 38 at its rear end remote to the opening 72 so that the latter is tightly sealed and only pipe 14 communicates with the interior of the tube 27. The supply line 14 as well as the sealing plug 26 are accommodated in a fitting 73 which radially extends from the housing 1 and is connected to a plate 74 at its end remote to the housing 1. The pipe 14 is fixedly connected to the plate 74.

The other axial end of the housing 1 remote from the flange 1a rests in a flange 42a which in turn is fixed, e.g. by screw connections, to a flange 42. By means of O-rings 75, the flanges 42, 42a are sealed against each other. Centered in the flange 42 is an emergency sealing and stop gland 12 which is provided with a centered through-hole 12a through which the piston rod 20 extends. A sealing between the piston rod 20 and gland 12 is obtained by four O-rings 76.

Figures 2, 3:
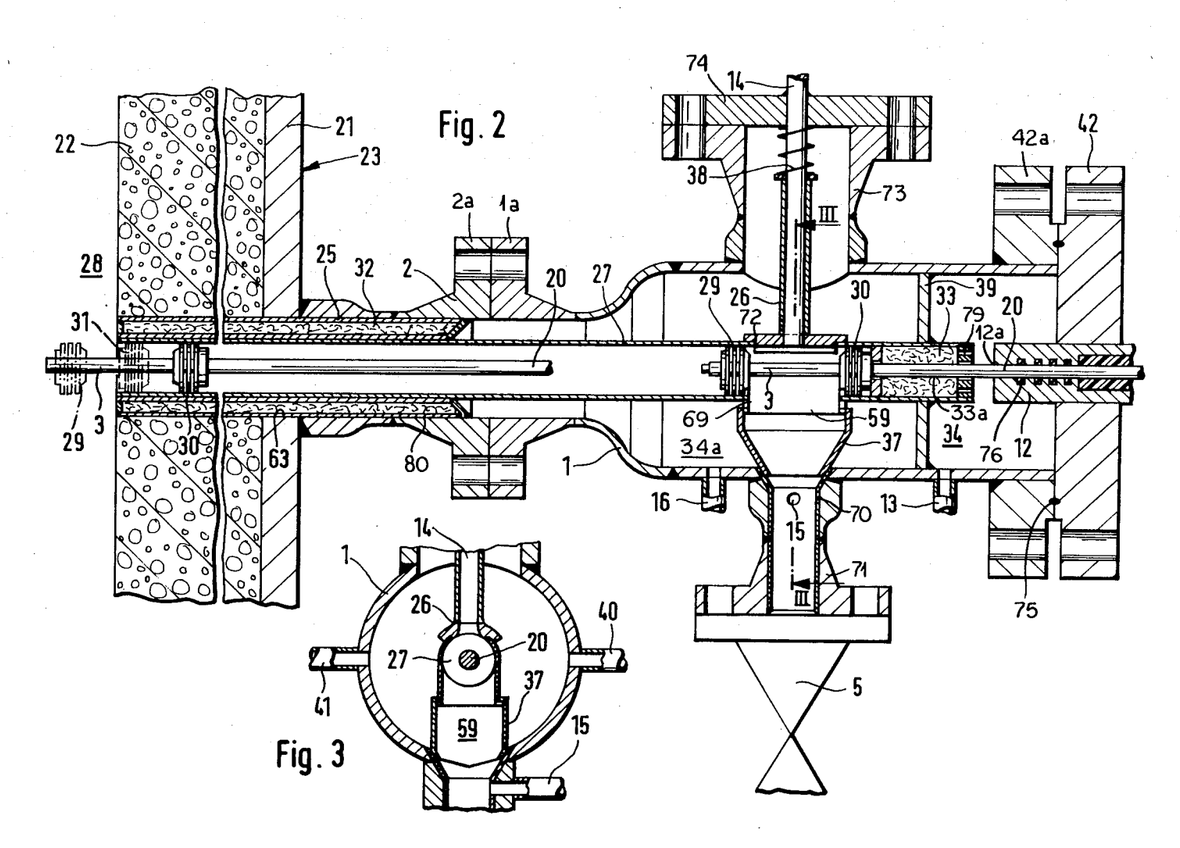
FIG. 2 is a cross-sectional view of a forward portion of the solids-extraction or sampling device.
FIG. 3 is a cross-sectional view taken along the line III—III in FIG. 2.

As can be seen from FIG. 2, the gland 12 projects into chamber 34 and opposes the respective end of the tube 27 which also partly projects into the chamber 34. Accommodated within this end of the tube 27 is a stuffing box 33 which is filled with highly temperature-resistant wool of $Al_2O_3$ and includes a central passage 33a through which the piston rod 20 passes. By using mineral wool, particles adhering to the piston rod 20 can be stripped off. The stuffing box 33 is provided at its end facing the chamber 34 with axial channels 79 through which the flushing and cooling gas enters in countercurrent flow into the filling to support the cleansing action.

By controlling the gas flow through the lines 14, 15, 16 as well as 40, 41, existing blockages (of accumulated solids) within the housing 1 or in the discharge areas 59, 37 can be eliminated. Moreover, aggressive (corrosive) crude gas fractions of the solids sample can be removed during transport through the tube 27 while being simultaneously cooled. In a normal situation, the supply of flushing and cooling gas is provided through the fitting 13 which gas—as already mentioned—served simultaneously as sealing for the gland 12 and stuffing box 33. The gas flows inside and outside of the tube 27 in direction towards the fluidized bed 28 and cools the solids sample as well as the tube 27 and the piston rod 20. In addition, the flow of the gas prevents a penetration of solids particles into the gap between the double-wall pipe 25 and the tube 27 so that a jamming thereof is avoided.

Figure 4:
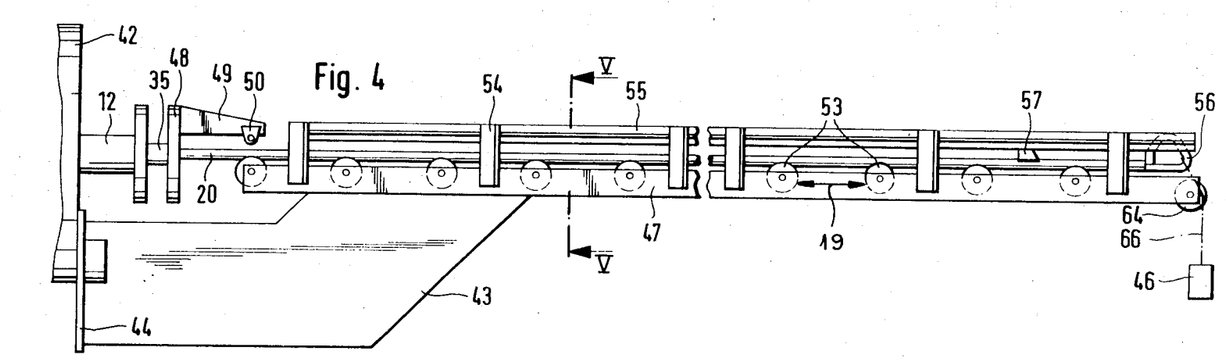
FIG. 4 is a side view of a rearward portion of the sampling device illustrating in particular the support for its piston rod.

Turning now to FIG. 4 which shows the support of the piston rod 20 outside the housing 1 as well as the drive mechanism for its back and forth movement within the tube 27, it may be seen that the gland 12 projects beyond the end flange 42 and is connected to a further end flange 48 via an intermediate gland 35.

Below the gland 12, a square holding plate 44 is connected to the flange 42 and carries two support arms 43 which extend parallel to each other. The arms 43 support a U-shaped roller support 47 which defines a roller path 19 for a plurality of rollers 53.

Figures 5, 6:
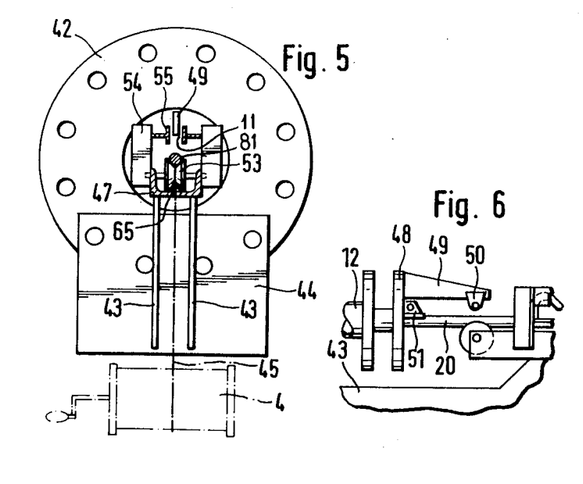
FIG. 5 is a cross-sectional view taken along the line V—V in FIG. 4.
FIGS. 6–8 each show a different position of the piston rod.

As is illustrated in FIG. 5, the rollers 53 define a central circumferential groove 81 in which the piston rod 20 is supported outside the pressure area of the sampling device 100. For reinforcing the roller path 19, along each shank of the roller support 47, a plurality of spaced holding blocks 54 are fixed thereto which support respective guide plates 55 extending parallel to the roller path 19 at a distance above the rollers 53. The guide plates 55 project inwardly towards each other to define a guide groove which serves as a guide for an eyelet 56 arranged at the axial end of the piston rod 20.

Fastened to the eyelet 56 is a rope (e.g. a wire rope or cable) 45 which is also guided by the rollers 53 and extends to a winch 4 along a guide groove 65 provided in the U-shaped support 47 (FIG. 5) by rotating the winch 4 e.g. by a handle 78, the back and forth movement of the piston rod 20 is controllable as the rope 45 is reeled on or wound off the winch 4. A counter weight 46 is also provided with its rope 66 fixed to the eyelet 56 via an end roller 64.

At a predetermined location, the piston rod 20 is provided with an upright projection 51 which limits the forward motion of the piston rod 20. The projection 51 cooperates also with a stop lug 50 which is arranged on the free end of a cantilever 49 whose other end is connected to the flange 48. As will be described hereinbelow, the projection 51 engages with the stop lug 50 when the piston rod 20 is in its idle position.

All parts of the sampling device 100 subjected to pressure are made of high tensile-strength steel, for example, VA-steel while those parts which are subjected to high temperature are made of heat-resistant steel, for example, Incoloy 800.

Figure 8:
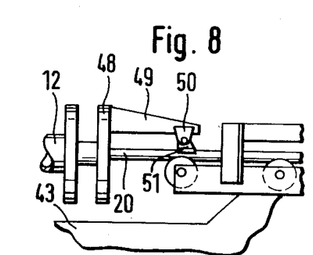
Figure 11:
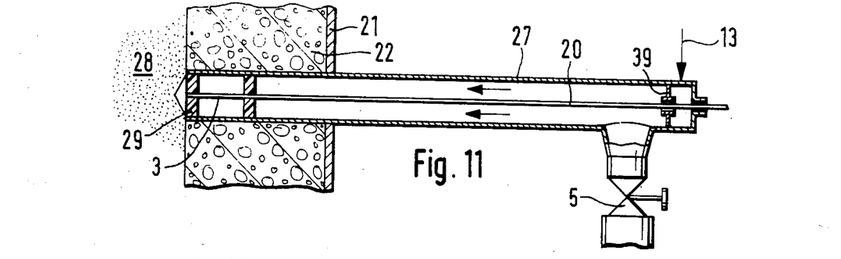
FIGS. 11–14 are diagrams which illustrate several successive positions of the sampling piston relative to the pressure reactor.
Figure 12:
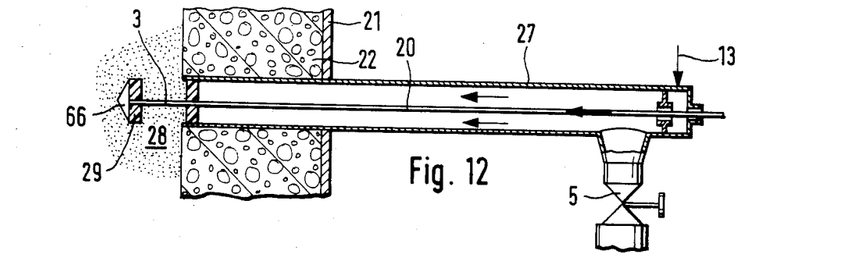

In the idle position of the sampling device 100, the piston rod 20 occupies a position in which the projection 51 engages with the stop lug 50 as shown in FIG. 8 while the front surface of piston ring 29 flushes approximately with the lining 22 (FIG. 11). Via line 13, flushing and cooling gas is supplied which provides a slight overpressure within the tube 27 with respect to the internal pressure in the fluidized bed 28, thereby preventing process gas and solids from penetrating into the tube 27. By actuating the winch 4, the piston rod 20 is moved forwardly so that the piston 3 projects into the fluidized bed 28. The length by which the piston 3 projects into the bed 28 can be controlled.

Figure 7:
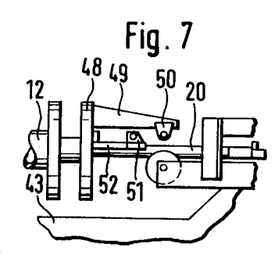

When the piston rod 20 is moved forwardly until its projection 51 abuts against the end flange 48 (FIG. 6—corresponding to a stroke of 85 mm), the piston 3 completely projects into the bed 28 as indicated in FIG. 2 in which the rear piston ring 30 is illustrated in dotted line 31 (compare the dot-dash position and the dotted line positions). It is, however, also possible to connect a spacer 52 to the end flange 48 so that the stroke of piston rod 20 is reduced, e.g. to 35 mm (FIG. 7). In this case, the piston 3 enters only partly the fluidized bed 28 as shown in FIG. 2. Thus, the quantity of solids to be removed is controllable. A penetration of process gas and solids into the interior of the tube 27 again is prevented by the overpressure of the gas.

To facilitate the forward motion of the piston 3 into the bed of solids, the front surface of the ring 27 can be provided with a push cone 66.

Figure 13:
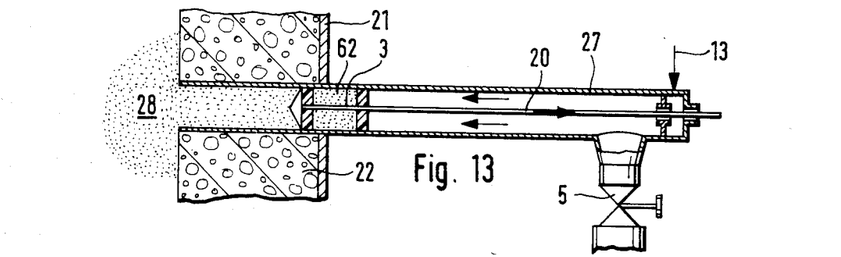
Figure 14:
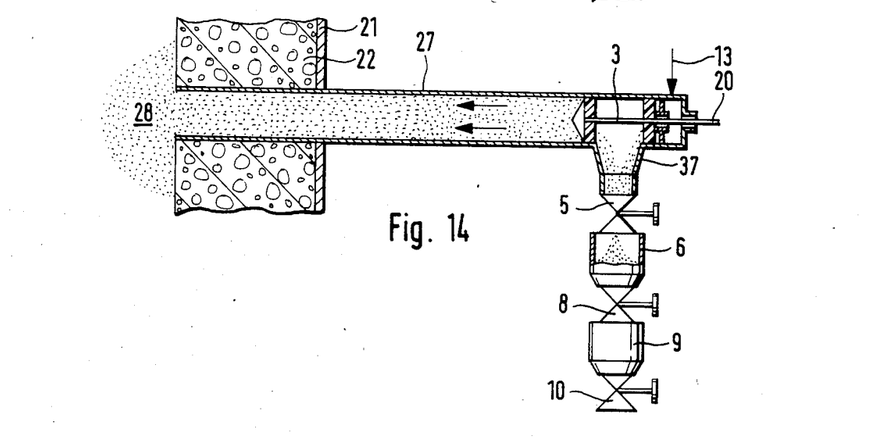

After being pushed into the bed 28, process pressure forces the piston 3 to move into the tube 27 with a sample 62 of solids arranged inbetween the piston rings 29, 30 (FIG. 13) until being positioned above the chamber 59 of the funnel 37 as illustrated in FIG. 2 by dashdot lines and in FIG. 14.

The retraction speed of the piston rod 20 is controlled by the winch 4 and can be 1 to 2 cm/s. During the rearward movement of the piston 3, no solids can be discharged into the solid-free section of the tube 27 because of the still prevailing overpressure of the gas which also cools the sample in countercurrent flow from approximately 850° C. temperature as prevailing in the fluidized bed 28 to about 8° C. In the present example, $N_2$ is used as the supplied gas. In addition, the gaseous component of the process which may penetrate into the tube 27 is returned to the bed 28 by the flushing and cooling gas.

When the piston 3 is located above the funnel 37, the solids sample 62 can drop into chamber 59. By opening the slider 5, the sample 62 flows into the first sluice 6 and via the second slider 8 into the second sluice 9, and finally is discharged via shutter 10. Thereafter, the piston 3 is returned to its initial position by means of the winch 4 at 40 bar with a winding force of about 80 kp. Consequently, solids entering the interior of the tube 27 during the backward motion of the piston 3 will be pushed back into the bed 28. Since the solids are fluidized along the circumference of the piston ring 29 by the flushing and cooling gas penetrating therebetween, the cleansing of the interior of tube 27 is obtained without seizing of the piston rings 29, 30.

SPECIFIC EXAMPLE

A sampling device 100 is used for a nominal pressure of PN=64 bar and a nominal width of DN=50 mm diameter and is mounted in the wall of a gas generator of a semi-industrial coal gasification plant. During the gasification, approximately one hundred solids samples are being withdrawn from the process chamber i.e. a coal-steam fluidized bed operated at maximal 850° C. and at a pressure of 40 bar. The tested sluice dimension allows an obtainable sample quantity of about 1100 ml solids. The sample is obtained during ten sliding cycles and then discharged. The required period is about 20 min. For urgent C-determinations, the discharge of one cycle with about 110 ml solids sample takes about 6 min.

The regulated amount of flushing and cooling gas amounts to 3 $m^3/h$ of $N_2$ of (STP). The following flow rates are obtained at the sampling piston 3:

(a) at the circumferential gap between piston plate 57 and tube 27: 46 cm/s (b) in the drawn sample between the piston rings 29,30: 1 cm/s.

These values allow the following statements:

to (a): The flow rate of 46 cm/s as provided in the piston area and which equal 2.3 times the loosening speed guarantees an unobjectionable returning of the solids by the "fluidized piston" once they enter the tube 27 during retraction of the piston 3. The simple loosening speed was determined in solids samples as withdrawn drawn from the fluidized bed. It was about 20 cm/s when air flows thereagainst. At a speed of 38 cm/s, complete fluidization of the sample is obtained.

to (b): At a flow rate of 1 cm/s within the piston rings 29, 30, no grain movement occurs in the sample and thus no loss of finest grain from the sample.

Obtained results of the solid material from the fluidized bed (40 bar, max. 850° C.).

In the following, we would like to show some test results concerning the grain size changes.

Table 1 shows the grain change during a batch reactor test. With progressing gasification to a degree of 56%, the mean grain triples. With further progressing gasification, the grain disintegrates again. At a gasification degree of 84%, the determined mean grain is 0.39 mm in this test. The results apply for the location at which the samples are withdrawn from the fluidized bed.

Table 2 illustrates the differences of the grain distribution between a directly withdrawn sample from the fluidized bed and a sample from the ash zone during the same test period.

TABLE 1

Gasification residue with varying gasification degree
Semi-industrial gasification plant
Feed Material: Gas flame coal Westerholt

| Gasification degree % | | 56.3 | 62.9 | 75.1 | 83.8 |
|---|---|---|---|---|---|
| Water % | | 3.4 | 5.1 | 3.0 | 3.7 | 0.4 |
| Ash % wf | | 5.0 | 12.0 | 13.0 | 17.9 | 32.8 |
| Liquid constituents % wf | | 34.0 | 0.9 | 1.0 | 1.1 | 1.3 |
| Carbon % wf | | 78.2 | 85.0 | 82.8 | 80.2 | 64.7 |
| Water % wf | | 5.07 | 1.18 | 1.03 | 1.06 | 0.78 |
| Nitrogen % wf | | 1.47 | 0.6 | 0.38 | 0.45 | 0.25 |
| Sulfur % wf | | 1.44 | 0.35 | 0.23 | 0.12 | 0.04 |
| Oxygen % wf | | 8.7 | 1.0 | 2.0 | 0.95 | — |
| Chlorine % wf | | — | <0.03 | <0.03 | <0.03 | 0.03 |
| Apparent density g/l | | 728 | 126 | 190 | 224 | 256 |
| Compacted apparent density g/l | | 892 | 143 | 217 | 260 | 300 |
| Ash-composition | | | | | | |
| SiO$_2$ % wf | | 41.4 | 42.2 | 41.7 | 44.4 | 43.3 |
| Al$_2$O$_3$ % wf | | 27.2 | 32.0 | 26.0 | 26.4 | 24.8 |
| TiO$_2$ % wf | | 1.0 | 1.0 | 1.1 | 0.9 | 0.7 |
| Fe$_2$O$_3$ % wf | | 25.0 | 16.5 | 19.0 | 16.0 | 18.7 |
| CaO % wf | | 1.7 | 2.4 | 2.4 | 2.6 | 2.2 |
| MgO % wf | | 0.4 | 0.7 | 1.5 | 2.3 | 2.2 |
| K$_2$O % wf | | 2.1 | 3.7 | 3.7 | 3.9 | 4.3 |
| SO$_3$ % wf | | 0.1 | n.n* | n.n* | n.n* | n.n* |
| P$_2$O$_5$ % wf | | 0.3 | 0.7 | 0.7 | 0.7 | 0.6 |
| Sieve analysis | | | | | | |
| 2–1% | | 0.5 | 47.8 | 15.8 | 9.0 | 2.1 |
| 1–0.8% | | 5.1 | 14.2 | 12.6 | 10.1 | 3.8 |
| 0.8–0.63% | | 7.8 | 14.0 | 16.0 | 13.7 | 10.4 |
| 0.63–0.5% | | 10.5 | 8.2 | 11.2 | 10.5 | 9.2 |
| 0.5–0.315% | | 19.5 | 9.2 | 19.4 | 17.7 | 21.4 |
| 0.315–0.2% | | 20.3 | 4.2 | 14.6 | 16.2 | 23.4 |
| 0.2–0.1% | | 16.0 | 2.0 | 9.6 | 16.6 | 25.6 |
| 0.1–0.063% | | 8.3 | 0.4 | 0.6 | 2.6 | 3.4 |
| 0.063–0.05% | | 2.8 | — | 0.2 | 1.0 | 0.4 |
| <0.05% | | 9.2 | — | — | 2.6 | 0.3 |
| mean grain diameter mm | | 0.34 | 1.02 | 0.66 | 0.53 | 0.39 |

Consequently, the mean grain size of the feed coal was 0.31 mm and the apparent density was 762 kg/m$^3$ for gas flame coal Westerholt. The mean grain of the direct sample from the fluidized bed was 0.53 mm and the apparent density 160.8 kg/m$^3$, while the mean grain of the sample from the ash zone was 0.36 mm and the apparent density was 480 kg/m$^3$.

During these tests, the gasification degree was 68% and the velocity in blower stream was 9.8 cm/s. The addition of catalysts was 4% K$_2$CO$_3$.

TABLE 2

| Mesh size (mm) | feed material gas flame coal Westerhold | sample directly of fluidized bed | sample of ash zone |
|---|---|---|---|
| 2.0–1.0 | | | |
| 1.0–0.8 | | | |
| 0.8–0.63 | 15.7 | 49.4 | 11.5 |
| 0.63–0.50 | 9.8 | 11.0 | 13.6 |
| 0.50–0.315 | 16.5 | 16.5 | 28.2 |
| 0.315–0.20 | 14.5 | 11.6 | 21.0 |
| 0.20–0.10 | 18.9 | 8.7 | 17.7 |
| 0.10–0.063 | 8.6 | 0.8 | 4.5 |
| 0.063–0.050 | 6.5 | 0.3 | 0.8 |
| <0.050 | 9.5 | 1.7 | 2.5 |
| mean grain dm | 0.31 | 0.53 | 0.36 |
| Apparent density kg/m$^3$ | 762.0 | 160.8 | 480.0 |

According to the present invention, it is technically possible to dimension and to build devices for discharge of solids samples withdrawn from process chambers of reactors with pressures ranging from 0 bar to far above 100 bar and temperatures greater than 1000° C. The obtainable sample quantity depends on the piston size and on the sluice size. For providing an improved operation, the piston movement can be motor-driven and the sluice system can be controlled by a control program. I may note that the piston can be operated in all directions. The sealing elements for the cooled sealing area in form of O-rings or sealing lips are conventional. Further, the sampling piston operating in high-temperature range can be made of ceramic material when very high temperatures (~130° C.) exist. In such cases, the piston rod should be internally cooled in a suitable manner. For extraction of samples from the solid bed, it is advantageous to provide the front portion of the piston ring 29 with a conical end, as indicated in FIGS. 11 to 14 in order to facilitate penetration into the bed.

We claim:

1. A sampling device for solids from a pressure reactor having a reactor wall, said sampling device comprising:
   a housing connected to the reactor and defining an axis;
   a tube in said housing extending through the reactor wall with one axial end opening into the reactor, said tube being provided with an outlet opening in said housing between ends of said tube
   a piston movable within said tube in an axial direction between a first position in which solids are withdrawn from the reactor and a second position in which said piston registers with said outlet opening;
   discharge means connected to said opening of said tube for allowing solids drawn from the reactor by said piston to be removed from said tube and said housing; and
   inlet and outlet means connected to said housing for providing a supply and discharge of at least one barrier flushing and cooling gas for said housing and said tube to block incursion of gas under pressure in said reactor, said piston including two spaced gas-permeable piston rings each of which has a plurality of spaced-apart plates and respective soft and elastic dust-trapping insulating layers arranged between each two successive plates of each of said rings.

2. A sampling device as defined in claim 1, further comprising a union, said housing being connected to the reactor via said union.

3. A sampling device as defined in claim 2, further comprising a double-wall pipe traversing said reactor wall and extending into said union, said double-wall pipe surrounding said tube to provide insulation for said tube in an area of high temperature.

4. A sampling device as defined in claim 1, further comprising a stuffing box in an axial end of said tube opposite said end opening into said reactor.

5. A sampling device as defined in claim 1, further comprising driving means for moving said piston between said positions, said driving means including a piston rod extending in axial direction with a forward end connected to said piston and with a rearward end extending from said housing, and a winch connected to said rearward end of said piston rod via a flexible element to move said piston rod in axial direction.

6. A sampling device as defined in claim 5, further comprising support means for guiding said rearward end of said piston rod, said support means including a roller track provided with a plurality of rollers which support said piston rod in axial direction.

7. A sampling device as defined in claim 6, further comprising O-rings and a gland for sealing and guiding said piston rod through said housing.

8. A sampling device as defined in claim 6, and further comprising stop means for limiting the forward movement of said piston rod towards the reactor.

9. A sampling device as defined in claim 1 wherein said housing has an outer wall, said discharge means including a funnel extending perpendicularly between said opening of said tube and said outer wall of said housing so as to define a chamber in alignment with said opening, a first slider connected to said outer housing wall and communicating with said chamber, a first sluice connected to said slider and provided with a gas supply line, a first shutter connected to said first sluice, a second sluice succeeding said first shutter and being provided with a gas expansion line, a second shutter connected to said second sluice and a collector arranged after said second sluice for accumulating the solids sample.

* * * * *